US012708394B2

(12) United States Patent
Tadano et al.

(10) Patent No.: US 12,708,394 B2
(45) Date of Patent: Aug. 18, 2026

(54) SURGICAL DEVICE

(71) Applicant: RIVERFIELD INC., Tokyo (JP)

(72) Inventors: Kotaro Tadano, Tokyo (JP); Koki Shindo, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 551 days.

(21) Appl. No.: 17/848,952

(22) Filed: Jun. 24, 2022

(65) Prior Publication Data

US 2022/0313299 A1 Oct. 6, 2022

Related U.S. Application Data

(63) Continuation of application No. PCT/JP2019/051046, filed on Dec. 25, 2019.

(51) Int. Cl.
*A61B 17/29* (2006.01)

(52) U.S. Cl.
CPC .. *A61B 17/2909* (2013.01); *A61B 2017/2905* (2013.01); *A61B 2017/2919* (2013.01); *A61B 2017/2937* (2013.01); *A61B 2017/2939* (2013.01)

(58) Field of Classification Search
CPC ..... A61B 34/70; A61B 34/71; A61B 17/2909; A61B 2017/2905; A61B 2017/2919; A61B 2017/2937; A61B 2017/2939; A61B 34/30; A61B 34/37; A61B 2034/301; A61B 2034/302; A61B 90/50; A61B 2090/506
USPC .......................................................... 606/205
See application file for complete search history.

(56) References Cited

U.S. PATENT DOCUMENTS

| | | | |
|---|---|---|---|
| 2002/0120252 A1* | 8/2002 | Brock | A61B 90/36 606/1 |
| 2003/0036748 A1 | 2/2003 | Copper et al. | |
| 2009/0112230 A1 | 4/2009 | Jinno | |
| 2015/0150635 A1 | 6/2015 | Kilroy et al. | |
| 2016/0135914 A1 | 5/2016 | Isoda | |
| 2017/0245848 A1* | 8/2017 | Berkelaar | A61B 17/00234 |
| 2017/0252096 A1 | 9/2017 | Felder et al. | |
| 2019/0328467 A1 | 10/2019 | Waterbury et al. | |

FOREIGN PATENT DOCUMENTS

| | | |
|---|---|---|
| JP | 2009-107087 A | 5/2009 |
| JP | 2011-072574 A | 4/2011 |
| JP | 4938753 B2 | 5/2012 |

(Continued)

OTHER PUBLICATIONS

Office Action issued Oct. 26, 2022 in European Application No. 19957427.8.

(Continued)

*Primary Examiner* — Kankindi Rwego
(74) *Attorney, Agent, or Firm* — Sughrue Mion, PLLC

(57) ABSTRACT

A surgical device includes a forceps device, driven portions to which a driving force is transmitted from outside the surgical device, plural wires, each being fixed to one of the driven portions and transmitting respective movements of the driven portions to the forceps device. The forceps device includes grasping portions that may be opened and closed by a movement of a first wire of the plural wires, and a joint portion that may be bent by a movement of one or more second wires of the plural wires.

18 Claims, 13 Drawing Sheets

(56) References Cited

FOREIGN PATENT DOCUMENTS

| | | | |
|---|---|---|---|
| JP | 2016-518160 | A | 6/2016 |
| WO | 2015/012023 | A1 | 1/2015 |
| WO | 2018/179140 | A1 | 10/2018 |
| WO | 2019/006087 | A3 | 1/2019 |

OTHER PUBLICATIONS

International Search Report for PCT/JP2019/051046, dated Feb. 25, 2020.

* cited by examiner 100
111
20
31
102
103
104
X
Y
Z 41 (41a)
41 (41b)
41 (41c)
23
Y
X
Z
35(35a)
24
35(35c)
21
31(31b)
31(31a)
31(31c)
35b
26(26b)
26(26c)
26(26a)
26(26d)
20
35(35c)
111

SURGICAL DEVICE

CROSS REFERENCE TO RELATED APPLICATION

This application is a continuation application of International Patent Application No. PCT/JP2019/051046, filed on Dec. 25, 2019, which is incorporated by reference herein in its entirety.

BACKGROUND

1. Field

The present disclosure relates to a surgical device.

2. Description of Related Art

For master-slave surgical robots, there have been demands for a technology for transmitting external forces acting on robotic forceps (surgical device) to an operator who operates the robot from an isolated place in order to improve safety and reduce the time for doctors to learn the operation. An external force transmitted to the operator is estimated on the basis of information such as the position and the driving force of an actuator, etc.

A related art method of transmitting a driving force generated by a driving source such as an actuator via wires to a surgical device to drive the surgical device tends to have a complicated mechanism.

SUMMARY

It is an aspect to provide a novel structure that relatively simply drives a surgical device.

According to an aspect of one or more embodiments, a surgical device may include a forceps device configured to perform a bending movement, and to perform opening and closing movements of grasping portions of the forceps device; a plurality of driven portions to which a driving force is transmitted from outside the surgical device; and a plurality of cords, each being fixed to one of the plurality of driven portions, the plurality of cords transmitting respective linear movements of the plurality of driven portions to the forceps device, wherein the forceps device includes a joint portion that performs the bending movement when a cord for the bending movement among the plurality of cords is pulled, and a link structure that performs the opening and closing movements when a cord for the opening and closing movements among the plurality of cords is moved.

According to another aspect of one or more embodiments, a surgical device may include a forceps device; a plurality of driven portions to which a driving force is transmitted from outside the surgical device; a plurality of wires, each being fixed to one of the plurality of driven portions, the plurality of wires transmitting respective movements of the plurality of driven portions to the forceps device, wherein the forceps device comprises a plurality of grasping portions configured to be opened and closed by a movement of a first wire of the plurality of wires; and a joint portion configured to bend by a movement of at least one second wire of the plurality of wires.

DETAILED DESCRIPTION

In a method of transmitting a driving force generated by a driving source such as an actuator via wires to a surgical device to drive the surgical device, wires are arranged between the driving source and the surgical device, and are adjusted to have a tension within a predetermined range. However, this method decelerates a rotating force of a motor via some gears and then drives the surgical device, which makes the mechanism complicated.

Figure 1:
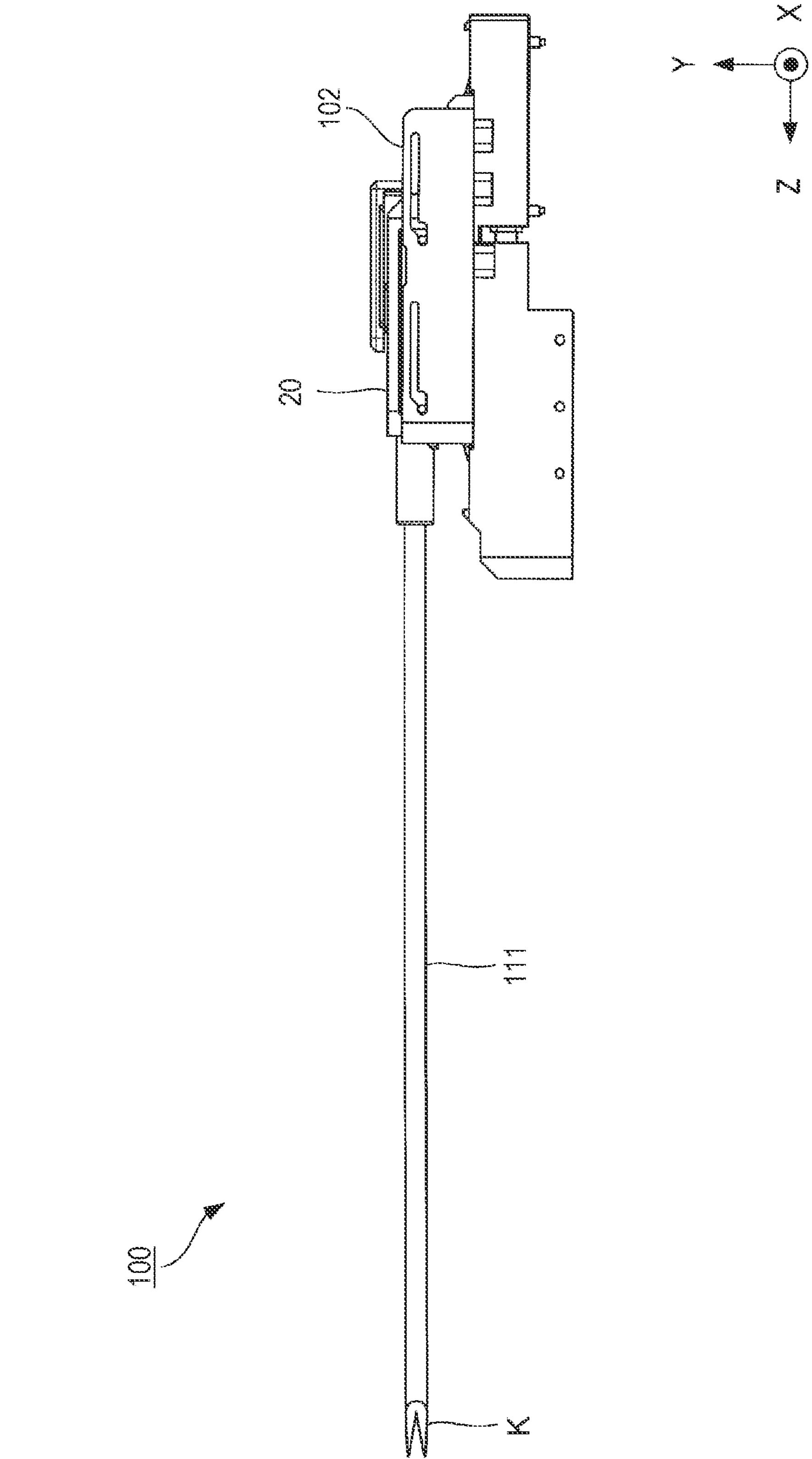
FIG. 1 is a drawing for explaining a structure of a surgical device according to an embodiment.
Figure 2:
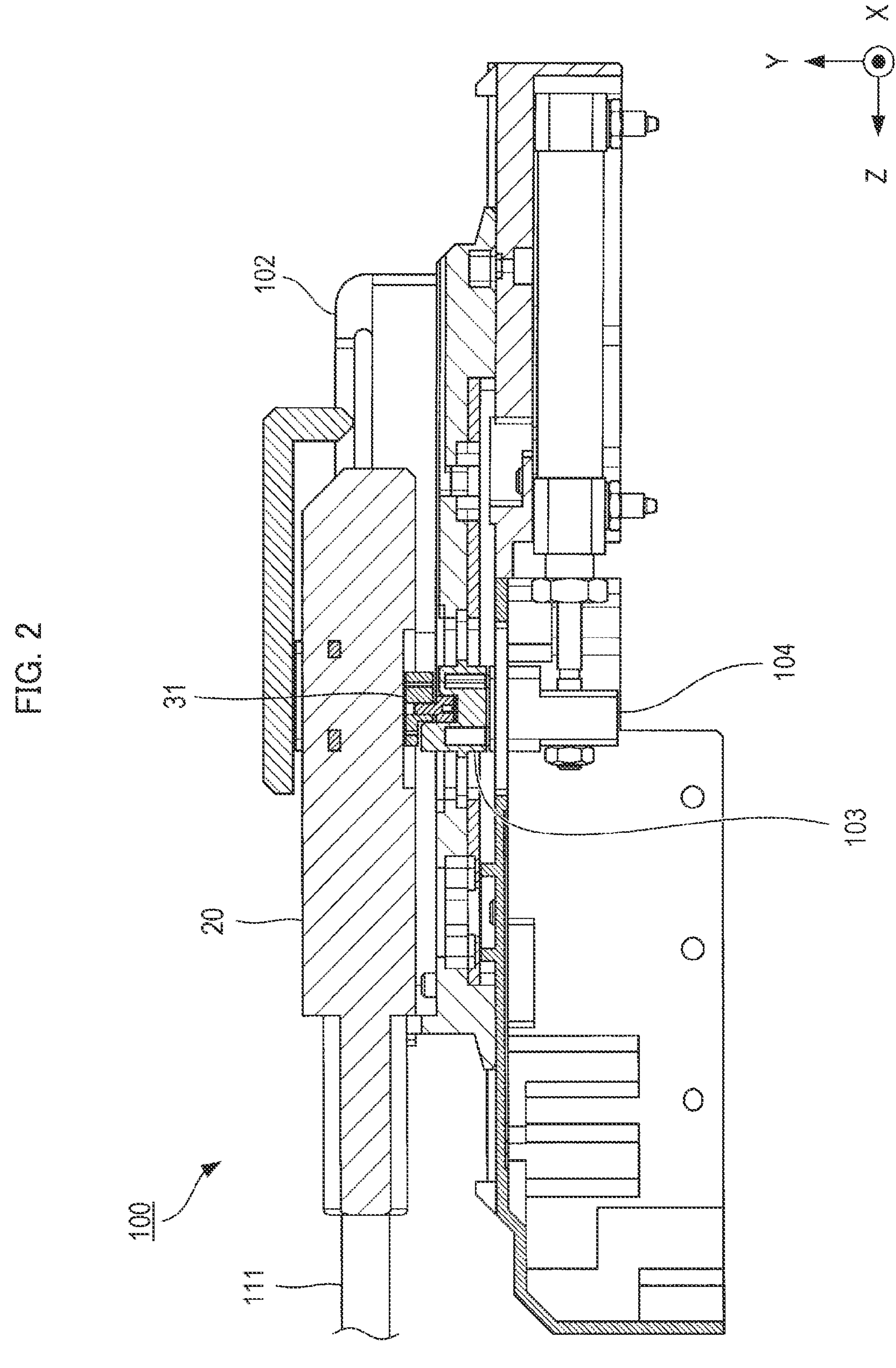
FIG. 2 is a partial cross-sectional view explaining an engaged state of the surgical device in FIG. 1 with an adapter, according to an embodiment.
Figure 3:
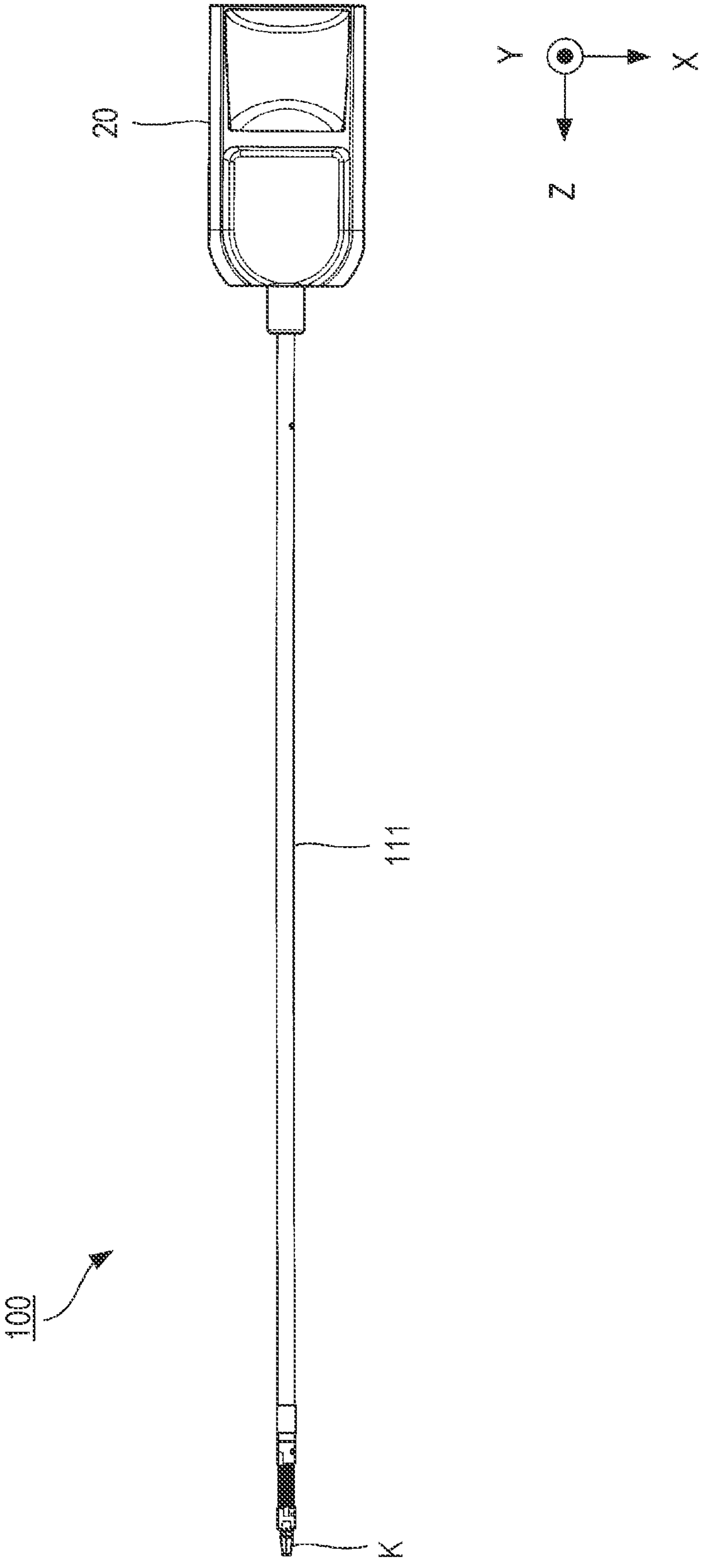
FIG. 3 is a perspective view explaining arrangement of a first housing part and a second housing part of the surgical device in FIG. 1, according to an embodiment.
Figure 4:
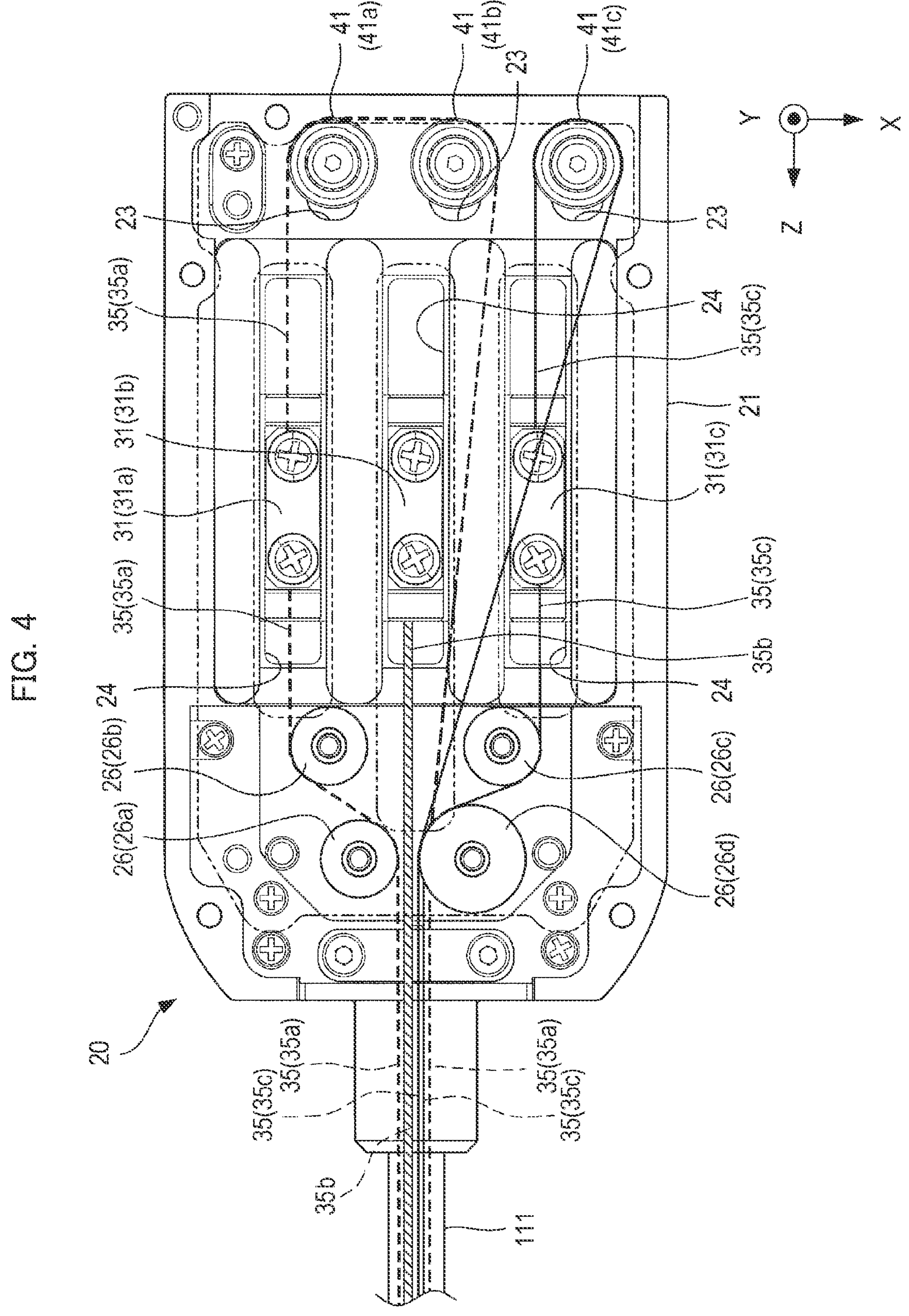
FIG. 4 is a top view explaining a structure inside a housing in FIG. 1, according to an embodiment.
Figure 5:
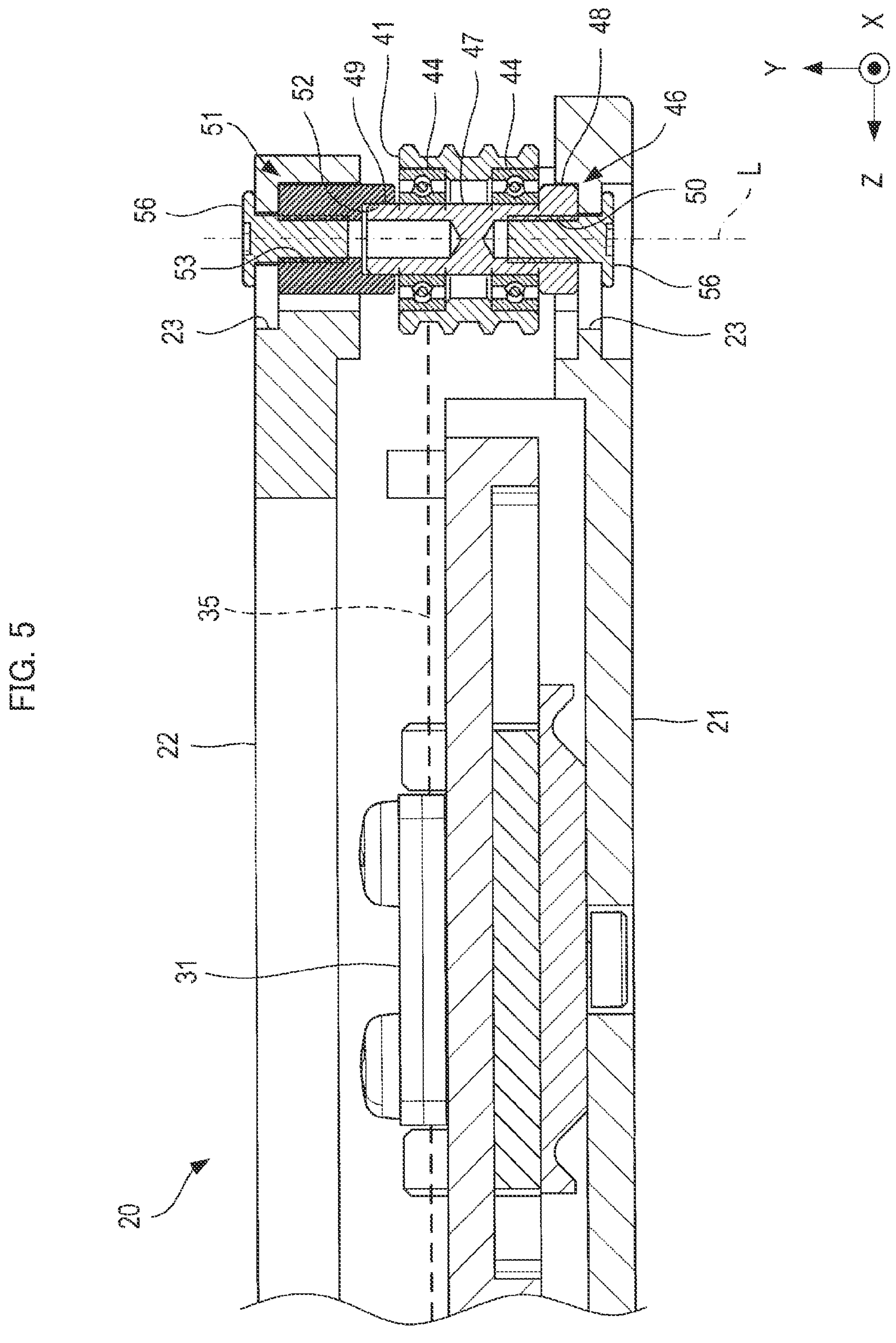
FIG. 5 is a partial cross-sectional view explaining the structure inside the housing in FIG. 1, according to an embodiment.

A surgical device 100 according to an embodiment will be described with reference to FIGS. 1 to 5. FIG. 1 is a drawing for explaining a structure of the surgical device according to an embodiment. FIG. 2 is a partial cross-sectional view explaining an engaged state of the surgical device FIG. 1 with an adapter, according to an embodiment. FIG. 3 is a perspective view explaining arrangement of a first housing part and a second housing part of the surgical device in FIG. 1, according to an embodiment. FIG. 4 is a top view explaining a structure inside a housing in FIG. 1, according to an embodiment. FIG. 5 is a partial cross-sectional view explaining the structure inside the housing in FIG. 1, according to an embodiment.

The surgical device 100 is to be applied to a master-slave surgical robot and to be used in operations. As described in FIG. 1, the surgical device 100 may include a shaft 111 having a leading end at which forceps device (operating part) K are located, and a housing 20 to be mounted on a surgical robot.

The shaft 111 is a member formed in a rod-like shape extending from the housing 20. The embodiment illustrated in FIG. 1 is described referring to application to an example in which the shaft 111 is a rod-shaped member extending in a Z-axis direction. A forceps device K, which is the operating part, is provided on the leading end, which is an end opposite the housing 20 (an end on a positive side of the Z axis), of the shaft 111. A space extending from the housing 20 to the forceps device K (along the Z-axis direction) is formed inside the shaft 111. A plurality of wires 35, which will be described later, may be arranged in the space.

As illustrated in FIG. 2, the housing 20 is attachable to and detachable from an adapter 102 of a surgical robot. Driving force for driving the forceps device K is transmitted from a power unit 104 to the housing 20 via a power transmission part (external) 103 of the adapter 102.

As illustrated in FIGS. 3 to 5, the housing 20 may include a first housing part (support part) 21, a second housing part (support part) 22, drive elements (driven portions) 31, the wires (cords) 35, pulleys (rotating members) 41, pulley rotating shafts (rotating shaft parts) 46, fixing blocks (fixing parts) 51, and fixing screws (fixing elements) 56.

As illustrated in FIGS. 4 and 5, the first housing part 21 and the second housing part 22 are plate-shaped members constituting at least part of the body of the housing 20. The embodiment illustrated in FIG. 2 will be described referring to application to an example in which the first housing part 21 is located on a side of the housing 20 facing the adapter 102 (a face on the Y axis negative side of the housing 20), and the second housing part 22 is located on a side of the housing 20 opposite the adapter 102 (a face on the Y axis positive side of the housing 20). In addition, the embodiment illustrated in FIG. 2 is described referring to application to an example in which the first housing part 21 and the second housing part 22 are parallel to the X-Z plane.

As illustrated in FIGS. 4 and 5, at least the wires 35, guide pulleys 26, the pulleys 41, the pulley rotating shafts 46, and the fixing blocks 51 are arranged between the first housing part 21 and the second housing part 22.

In regions near the ends of the first housing part 21 and the second housing part 22 on a side opposite the shaft 111 (on the Z axis negative side), long holes 23 for pulley used for arrangement of the pulleys 41 are formed.

The long holes 23 for pulley are through-holes extending toward the shaft 111 side (the Z axis positive side) of the first housing part 21 and the second housing part 22. In other words, the long holes 23 for pulley are long holes extending along the Z-axis direction. The embodiment illustrated in FIGS. 4-5 is described referring to application to an example in which three long holes 23 for pulley are arranged in the X-axis direction with a space therebetween. Alternatively, the number of long holes 23 for pulley may be more than or less than three.

The first housing part 21 has long holes 24 for driving in which the drive elements 31 are disposed. The long holes 24 for driving allow movement of the drive elements 31 in a direction along the first housing part 21, and restrict movement thereof in a direction away from the first housing part 21 (the Y-axis direction).

The long holes 24 for driving are located at positions on the first housing part 21 closer to the shaft 111 than the long holes 23 for pulley are. For example, the long holes 24 for driving are located in a central region in the Z-axis direction of the first housing part 21.

The long holes 24 for driving are through-holes extending linearly toward the shaft 111 side (the Z axis positive side). In other words, the long holes 24 for driving are long holes extending along the Z-axis direction. The embodiment illustrated in FIGS. 4-5 is described referring to application to an example in which three long holes 24 for driving are arranged in the X-axis direction with a space therebetween. Alternatively, the number of long holes 24 for driving may corresponds to the number of long holes 23 for pulley, and may be more than or less than three.

The embodiment illustrated in FIGS. 4-5 is described referring to application to an example in which three long holes 24 for driving have an equal length in the Z-axis direction. Note that the lengths in the Z-axis direction of the three long holes 24 for driving may be equal to each other as mentioned above, or may be different from each other.

The guide pulleys 26 guide the wires 35, which extend from the drive elements 31 to the shaft 111, into an internal space of the shaft 111. More specifically, the guide pulleys 26 guide the wires 35, which extend from the drive elements 31 each located on the positive side or the negative side in the X-axis direction with respect to the shaft 111 with a space from the shaft 111, to the shaft 111.

As illustrated in FIGS. 4 and 5, the guide pulleys 26 are arranged in an end region on the shaft 111 side (on the Z axis positive side) between the first housing part 21 and the second housing part 22. In other words, the guide pulleys 26 are arranged between the long holes 24 for driving and the shaft 111 in a space between the first housing part 21 and the second housing part 22.

The guide pulleys 26 are attached to at least one of the first housing part 21 and the second housing part 22, and are each rotatable about an axis along the Y-axis direction. The shapes and structures of the guide pulleys 26 are not particularly limited.

As illustrated in FIGS. 4 and 5, the drive elements 31 receives driving force transmitted from the power transmission part 103 of the adapter 102, and transmit the transmitted driving force to the wires 35. The drive elements 31 are caused to reciprocate along the long holes 24 for driving by the driving force transmitted from the power transmission part 103.

The face of each drive element 31 facing the long hole 24 for driving has a projecting and recessed shape that allows relative movement of the element 31 along the first housing part 21 and restricts movement thereof away from the first housing part 21. Each long hole 24 for driving has a projecting and recessed shape to be engaged with the projecting and recessed shape of the drive element 31. Note that the projecting and recessed shapes are not particularly limited.

Furthermore, a region of each drive element 31 facing the power transmission part 103 has a projecting and recessed shape used for transmission of the driving force. The projecting and recessed shape is a shape allowing the drive elements 31 and the power transmission part 103 to be engaged with and separated from each other in the Y-axis direction. Note that the projecting and recessed shape is not particularly limited.

The wires 35 transmit the driving force transmitted to the drive elements 31 to the forceps device K. In other words, the wires 35 transmit the movement of the drive elements 31 to the forceps device K. The material and the shape of the wires 35 are not particularly limited.

A wire 35 that extends from a drive element 31 in the Z-axis negative direction is wound around a pulley 41. After being wound around the pulley 41, the wire 35 extends in the Z-axis positive direction and is guided into the shaft 111.

A wire 35 that extends in the Z-axis positive direction from a drive element 31 that is located away from the shaft 111 in the X-axis direction, for example, is wound around a guide pulley 26 and guided into the shaft 111.

The wires 35 that are guided into the shaft 111 transmit the driving force to the forceps device K. The structure for transmitting the driving force may be, for example, a structure in which the end of each of the wires 35 guided into the shaft 111 may be attached to the forceps device K, or the ends of the respective wires 35 may be connected in a loop shape and wound around a pulley in the forceps device K. The connection between forceps and each wire will be described with reference to a forceps device, which will be describe later.

The pulleys 41 are members formed in a cylindrical shape having a circumferential face around which a wire 35 is wound. Each pulley 41 changes the direction of a wire 35 extending from a drive element 31 in the Z-axis negative direction to the Z-axis positive direction.

Each of the pulleys 41 is arranged in a long hole 23 for pulley with a pulley rotating shaft 46, a fixing block 51, and a fixing screw 56. In other words, the pulleys 41 are positioned so that the drive elements 31 are between the shaft 111 on which the forceps device K is provided and the pulleys 41.

Each of the cylindrical pulleys 41 has a length in the central axis direction, that is, a height in the Y-axis direction shorter (lower) than the distance between the first housing part 21 and the second housing part 22.

The internal space of each cylindrical pulley 41 is a space in which the pulley rotating shaft 46 is located, and bearings 44 that support the pulley 41 so that the pulley 41 is rotatable about the rotation axis L are disposed between the pulley 41 and the pulley rotating shaft 46. Note that the central axis of the pulley 41 is coincident with the rotation axis L.

The circumferential face of each cylindrical pulley 41 has three annular grooves arranged at regular intervals in the central axis direction of the pulley 41 (the Y-axis direction). The embodiment illustrated in FIGS. 4-5 is described referring to application to an example in which the grooves have a width equal to a length corresponding to the width of two wires 35 arranged adjacent to each other. Alternatively, the width of each of the grooves may be larger or smaller than the width of two wires 35 arranged adjacent to each other.

Each of the pulleys 41 further has two cutouts connecting adjacent grooves. The cutouts are formed by cutting off portions of ridge-like projections defining adjacent grooves, and each have a width allowing a wire 35 to extend from one groove to another. The embodiment illustrated in FIGS. 4-5 is described referring to application to an example in which two cutouts are arranged at the same phase on the circumferential face of the pulley 41. Note that the two cutouts may be arranged at the same phase, or may be arranged at different phases from each other.

As illustrated in FIG. 5, the pulley rotating shafts 46 are each a member formed in a cylindrical or columnar shape that rotatably supports the pulley 41. Each of the pulley rotating shafts 46 may include an insertion portion 47 inserted through the bearings 44 disposed in the internal space of the pulley 41, and an enlarged diameter portion 48 disposed at one end of the insertion portion 47. A leading end (projecting portion) 49 of the insertion portion 47 is to be inserted in a recessed portion 52 of a fixing block 51, which will be described later.

The enlarged diameter portion 48 has a shape with a diameter larger than the inner diameter of the bearings 44 through which the insertion portion 47 is inserted. The pulley rotating shafts 46 each have a length with which an end of the insertion portion 47 and an end of the enlarged diameter portion 48 stick out from the pulley 41 in a state in which the insertion portion 47 is inserted through the bearings 44 and the enlarged diameter portion 48 is in contact with one of the bearings 44.

An end of each pulley rotating shaft 46 has a screw hole 50, which is to be engaged with the fixing screw 56, on an end face thereof adjacent to the enlarged diameter portion 48. The screw hole 50 is located on the central axis of the cylindrical or columnar pulley rotating shaft 46. Note that the screw hole 50 may be a hole extending through the pulley rotating shaft 46 or may be a bottomed hole.

The fixing blocks 51 are each a member formed in a cylindrical or columnar shape that supports the pulley rotating shaft 46 and the pulley 41. The end of each fixing block 51 adjacent to the pulley rotating shaft 46 has the recessed portion 52 in which the leading end 49 of the insertion portion 47 is inserted, and the opposite end of the fixing block 51 has a screw hole 53 to be engaged with the fixing screw 56.

While the embodiment illustrated in FIG. 5 is described referring to application to an example in which the recessed portion 52 is formed on the fixing block 51 and the leading end 49 of the insertion portion 47 is inserted in the recessed portion 52, alternatively, a recessed portion may be formed on the insertion portion 47 and a projecting portion formed on the fixing blocks 51 may be inserted in the recessed portion.

The fixing block 51 is located between the leading end 49 of the pulley rotating shaft 46 and the second housing part 22. The fixing block 51 may move in the Z-axis direction relative to the second housing part 22, and may be fixed. In addition, the position of the fixing block 51 relative to the pulley rotating shaft 46 may be changed along the Y-axis direction, and the movement of the fixing block 51 in the X-axis direction and the Z-axis direction relative to the pulley rotating shaft 46 is restricted.

As illustrated in FIG. 5, the fixing screw 56 is an external thread inserted in the long hole 23 for pulley, and screwed with the pulley rotating shaft 46 and the fixing block 51. The first housing part 21 is sandwiched between the fixing screw 56 screwed in the screw hole 50 of the pulley rotating shaft 46 and the pulley rotating shaft 46, and the fixing screw 56 presses the pulley rotating shaft 46 against the first housing part 21 and thus fixes the pulley rotating shaft 46. The second housing part 22 is sandwiched between the fixing screw 56 screwed in the screw hole 53 of the fixing block 51 and the fixing block 51, and the fixing screw 56 presses the fixing block 51 against second housing part 22 and thus fixes the fixing block 51.

Next, the operation of the surgical device 100 having the structure described above will be explained. As illustrated in FIG. 2, the driving force for driving the forceps device K of the surgical device 100 is transmitted from the power unit 104 to the drive elements 31 via the power transmission part 103 of the adapter 102. As illustrated in FIGS. 2 and 4, the drive elements 31 reciprocate along the long holes 24 for driving in the Z-axis direction relative to the housing 20.

The movement of the drive elements 31 is transmitted to the wires 35. Each wire 35 reciprocates along a direction in which the wire 35 extends. A wire 35 that extends from a drive element 31 toward the forceps device K (on the positive side of the Z-axis direction) reciprocates along the directions in which the wire 35 is guided by a guide pulley 26. A wire 35 that extends from a drive element 31 toward a pulley 41 (on the negative side in the Z-axis direction) reciprocates along the directions in which the wire 35 is guided by a pulley 41 and a guide pulley 26.

The wires 35 extend through the internal space of the shaft 111 to the forceps device K, and the reciprocating movements of the wires 35 are transmitted to the forceps device K. The forceps device K performs opening and closing movements on the basis of the reciprocating movements of the wires 35. While the embodiment illustrated in FIGS. 1-5 is described referring to application to an example in which the forceps device K performs a bending movement for changing the orientation thereof on the basis of the reciprocating movements of the wires 35, the forceps device K may also perform other movements such as opening and closing movements of gasping portions thereof.

In the embodiment illustrated in FIGS. 1-5, two wires (two braided wires) are provided to achieve two bending movements of the forceps. Furthermore, one cable is provided, in addition to the two wires, to achieve one opening and closing (pinching) movement of the forceps. The layout of the wires and the cable in the housing will now be described.

A wire 35*a* has one end or a portion fixed to one side, closer to the forceps device K, of a drive element 31*a*, and the other end or another portion fixed to the other side, closer to the pulleys 41, of the drive element 31*a*. The wire 35*a* extending from the side, closer to the forceps device K, of the drive element 31*a* is passed over guide pulleys 26*a* and 26*b*, and guided to the internal space of the shaft 111. In addition, the wire 35*a* extending from the side, closer to the pulleys 41, of the drive element 31*a* is passed over pulleys 41*a* and 41*b* and a guide pulley 26*d*, and guided to the internal space of shaft 111.

A cable 35*b* has one end fixed to one side, closer to the forceps device K, of a drive element 31*b*. The cable 35*b* extending from the side, closer to the forceps device K, of the drive element 31*b* is directly guided to the internal space of shaft 111.

A wire 35*c* has one end or a portion fixed to one side, closer to the forceps device K, of a drive element 31*c*, and the other end or another portion fixed to the other side, closer to the pulleys 41, of the drive element 31*c*. The wire 35*c* extending from the side, closer to the forceps device K, of the drive element 31*c* is passed over guide pulleys 26*c* and 26*d*, and guided to the internal space of shaft 111. In addition, the wire 35*c* extending from the side, closer to the pulleys 41, of the drive element 31*c* is passed over a pulley 41*c* and the guide pulley 26*d*, and guided to the internal space of shaft 111.

Note that each of the pulleys illustrated in FIG. 4 is actually one of a plurality of pulleys, which overlap each other in the drawing, having a common axis. The wires are passed over different pulleys that overlap each other. In other words, no more than one wire may be passed over each groove of the pulleys.

<Forceps Device>

Figure 6:
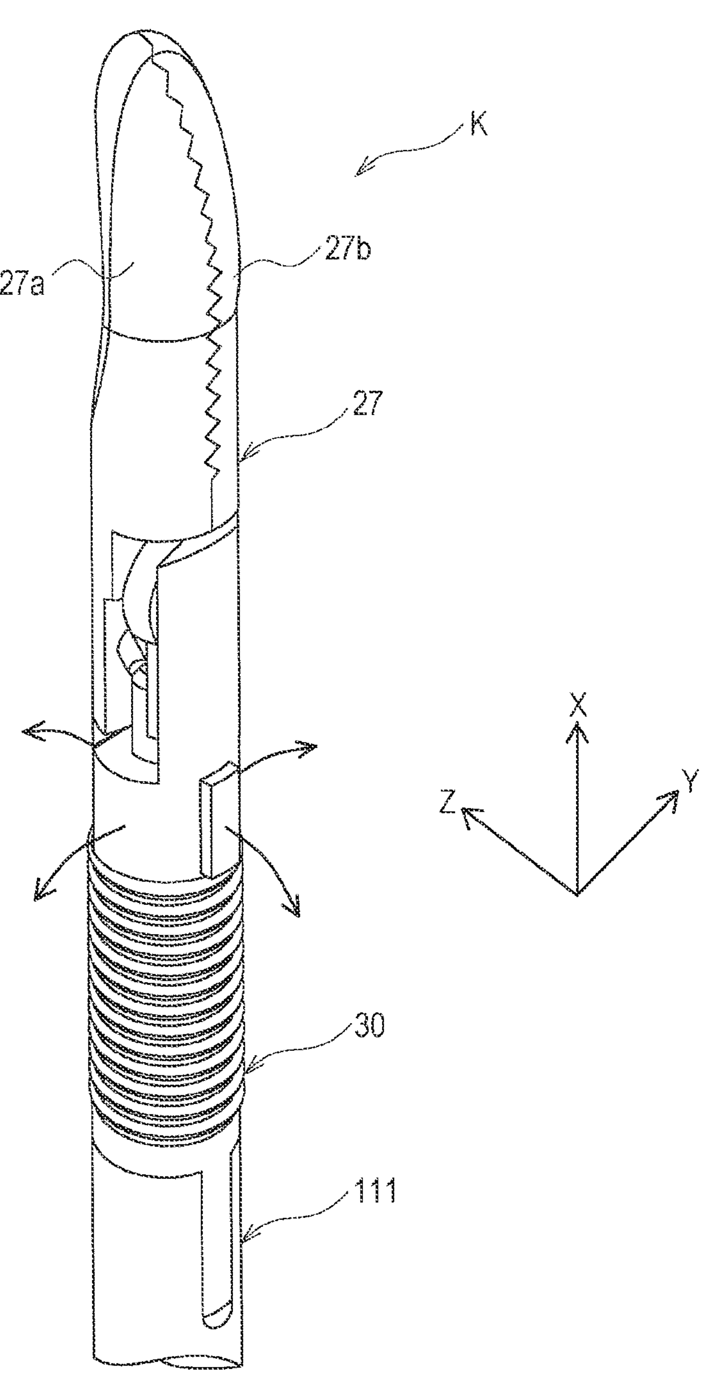
FIG. 6 is a perspective view illustrating part of a forceps device, according to an embodiment.
Figure 7:
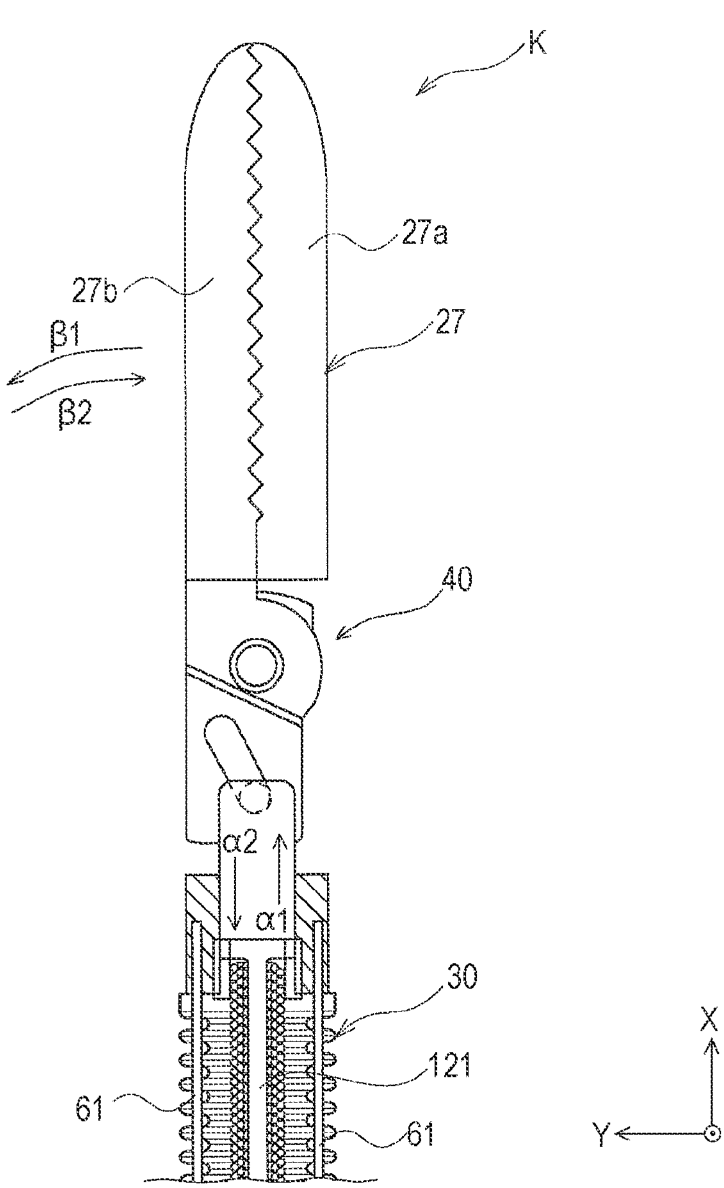
FIG. 7 is a schematic view of a cross-section of the forceps device illustrated in FIG. 6, according to an embodiment.

Next, the forceps device according to an embodiment will be described in detail with reference to the drawings where appropriate. FIG. 6 is a perspective view illustrating part of the forceps device according to an embodiment. FIG. 7 is a schematic view of a cross section of the forceps device illustrated in FIG. 6, according to an embodiment. The forceps device of the embodiment illustrated in FIGS. 6-7 constitutes a robot arm leading end of a surgical robot, which is a medical manipulator.

Note that the forceps device K is an example of a device having a bendable joint portion. The forceps device K includes a shaft 111, a joint portion 30, and a grasping unit 27, which is a surgical end effector.

In addition, the forceps device K having the joint portion 30 is structured to be capable of bending the grasping unit 27 in a plurality of directions and performing opening and closing movements of two grasping portions 27*a* and 27*b* of the grasping unit 27 by using a cable 121 for the surgical device and wires 61 for the joint portion extending through the inside of the forceps device K.

<Joint Portion>

Figure 8:
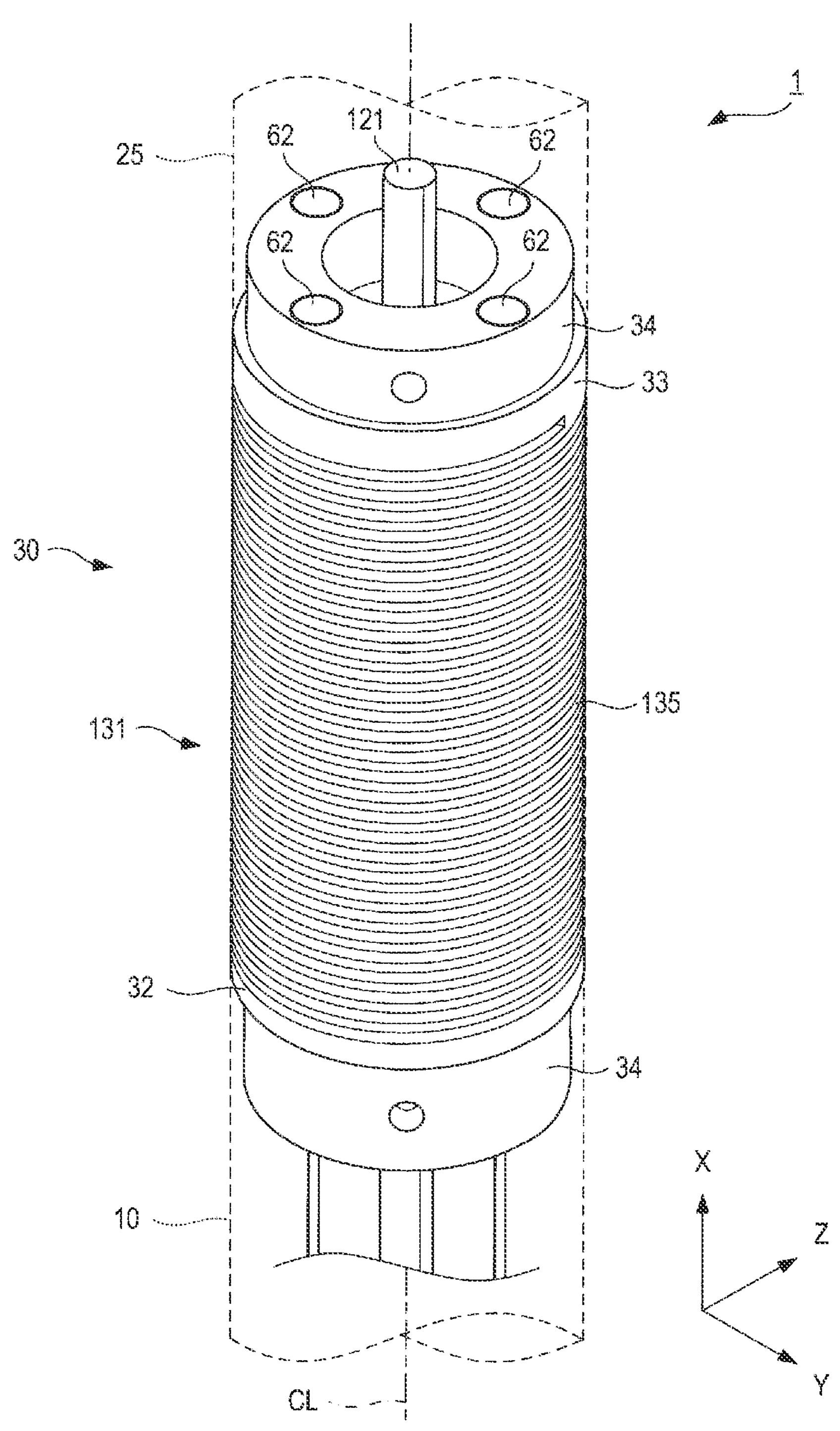
FIG. 8 is a perspective view for explaining the entire structure of a medical device, according to an embodiment.
Figure 9:
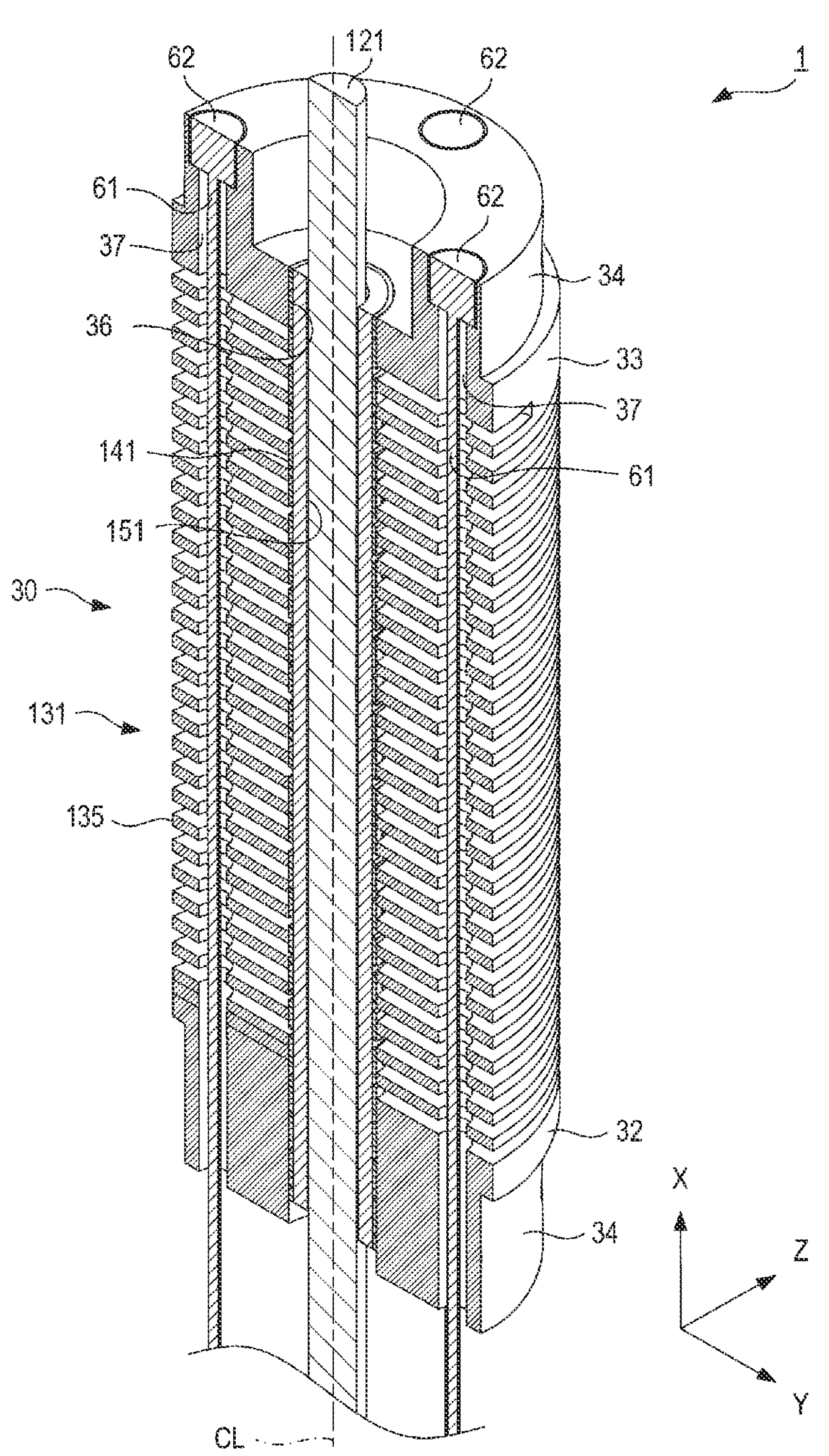
FIG. 9 is a cross-sectional view for explaining the structure of a joint portion in FIG. 8, according to an embodiment.
Figure 10:
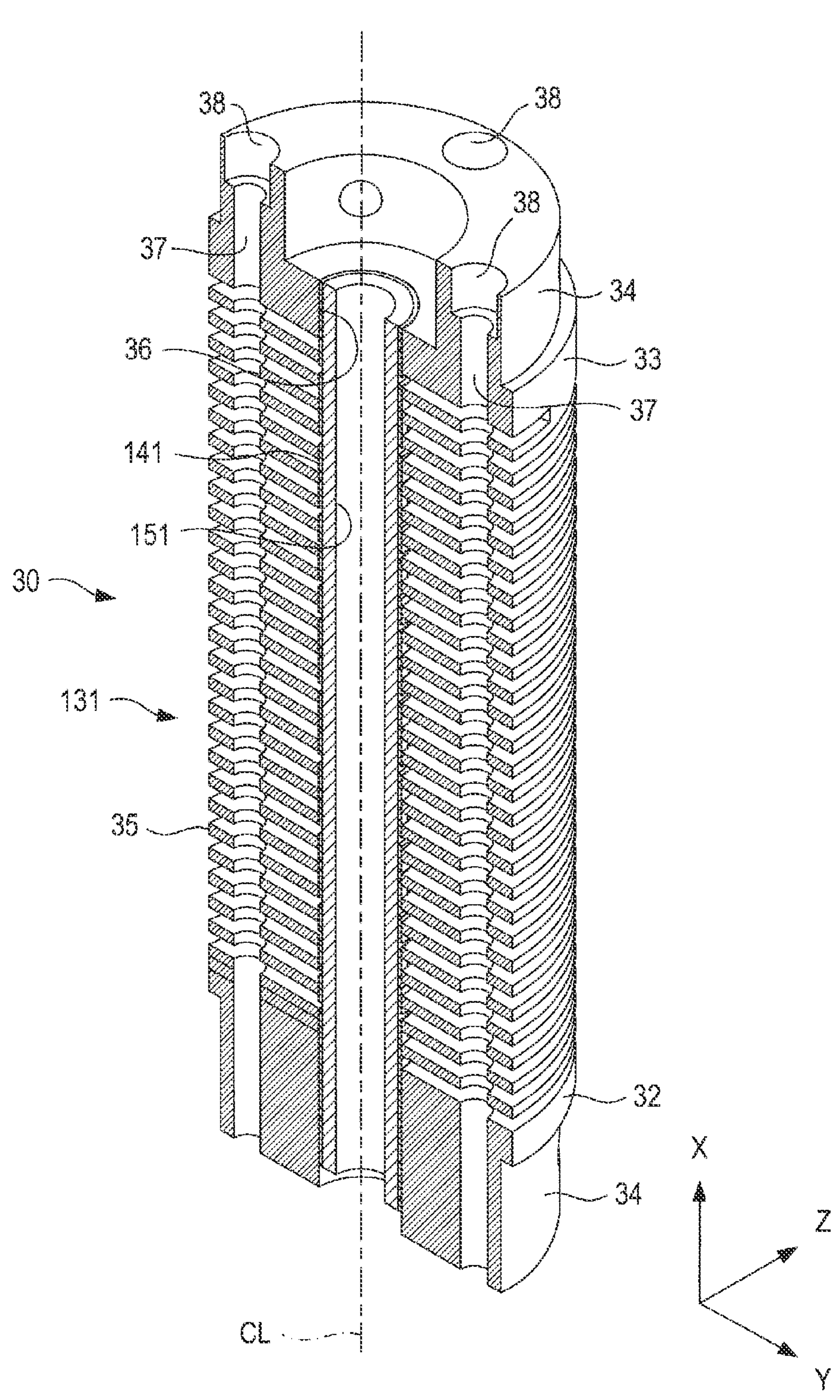
FIG. 10 is a partial cross-sectional view for explaining the structure of the joint portion in FIG. 8, according to an embodiment.
Figure 11:
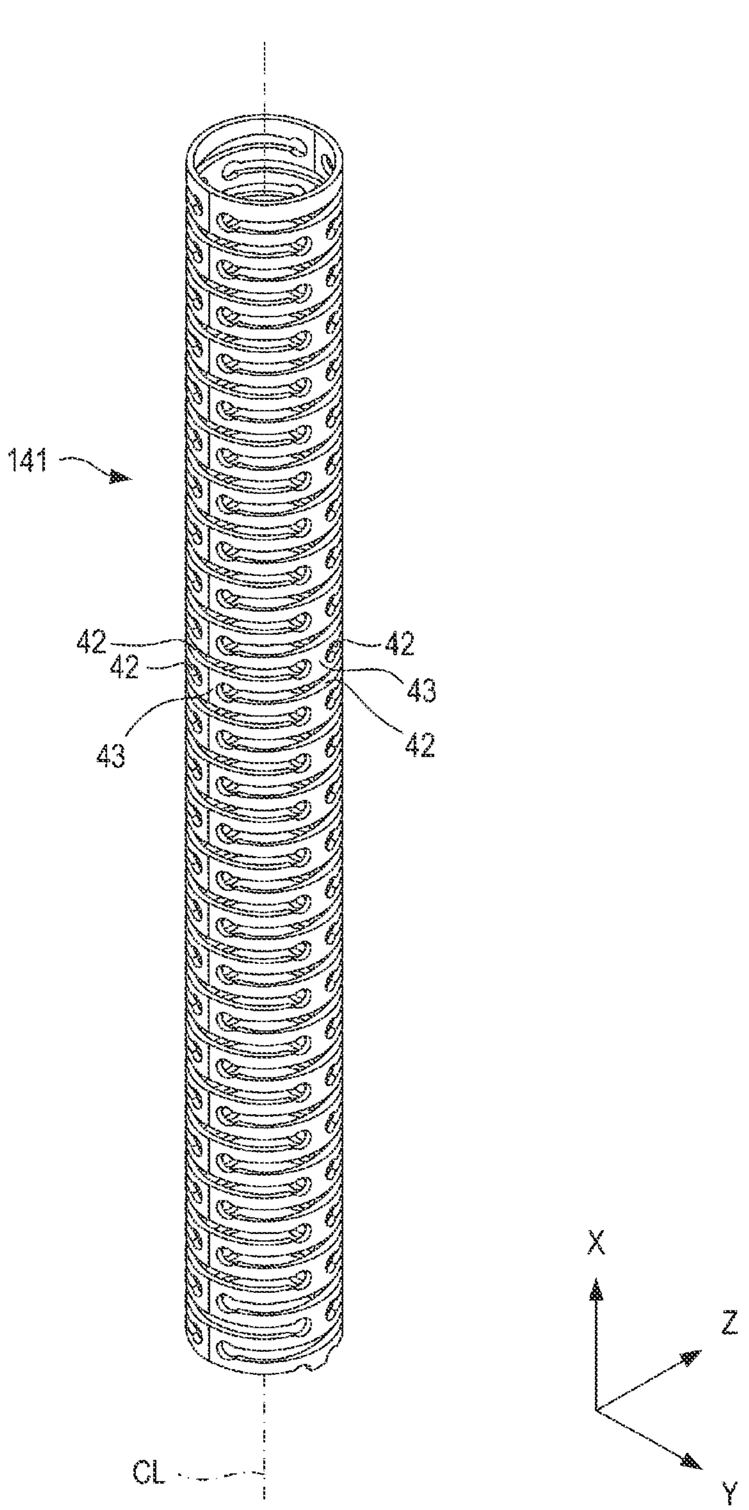
FIG. 11 is a perspective view for explaining the structure of a core tube in FIG. 10, according to an embodiment.
Figure 12:
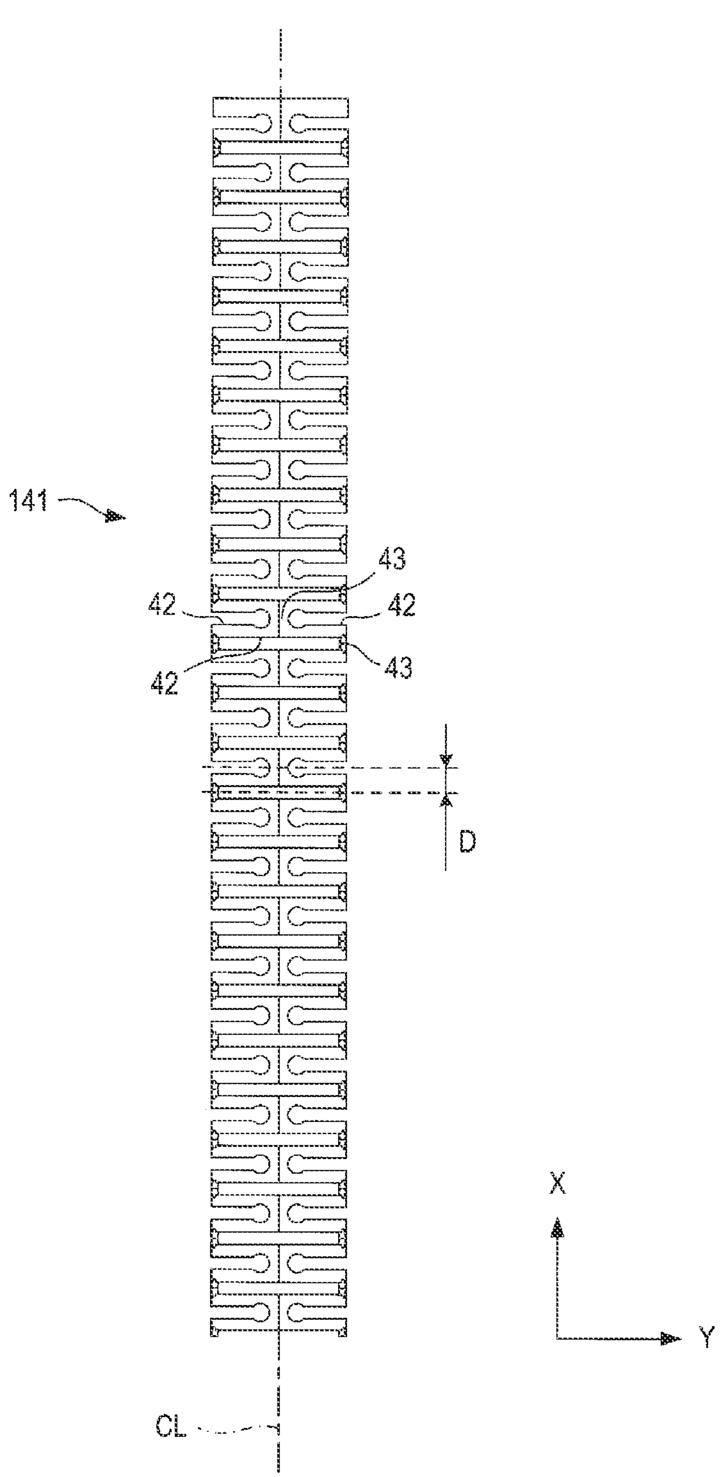
FIG. 12 is a front view explaining the structure of the core tube in FIG. 10, according to an embodiment.
Figure 13:
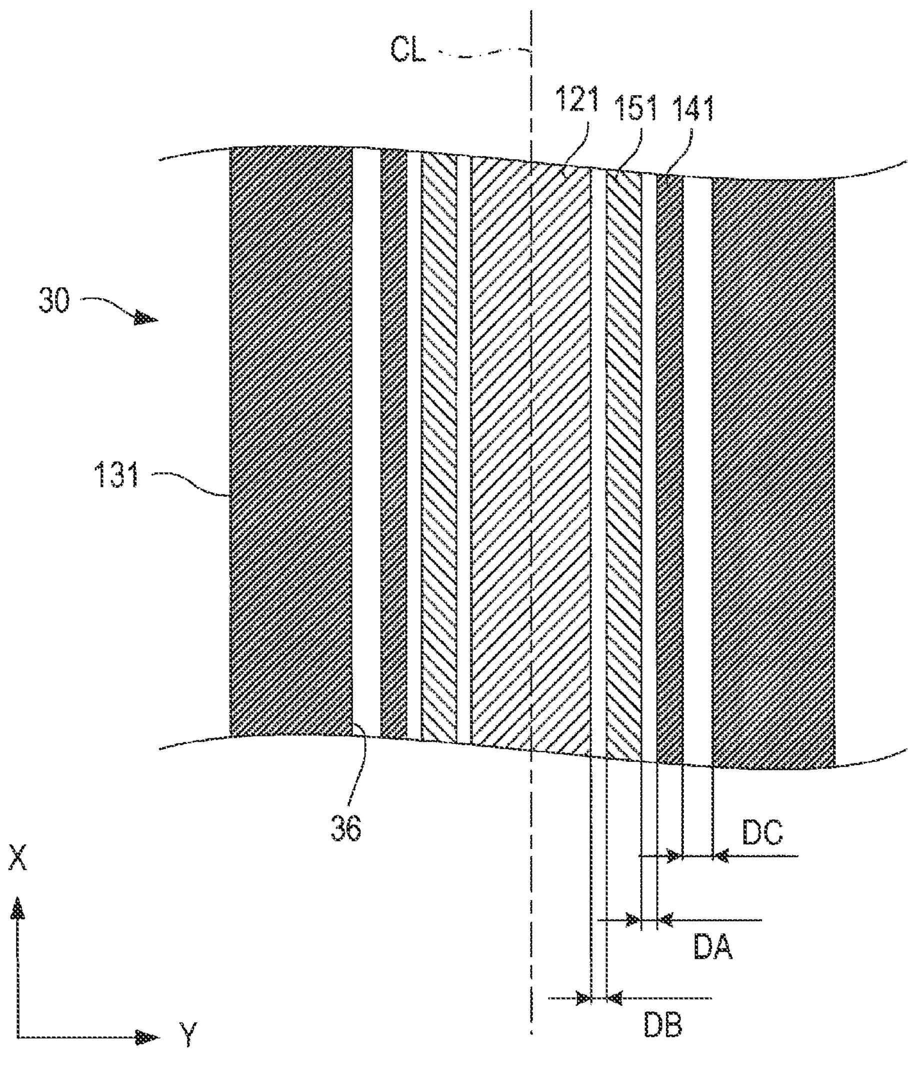
FIG. 13 is a schematic cross-sectional view explaining the relation of a plurality of gaps in the joint portion, according to an embodiment.

Next, a medical device 1 having a joint portion according to an will be described with reference to FIGS. 8 to 13. FIG. 8 is a perspective view for explaining the entire structure of the medical device according to an embodiment. FIG. 9 is a cross-sectional view for explaining the structure of the joint portion in FIG. 8, according to an embodiment. FIG. 10 is a partial cross-sectional view for explaining the structure of the joint portion in FIG. 8, according to an embodiment. FIG. 11 is a perspective view for explaining the structure of a core tube in FIG. 10, according to an embodiment. FIG. 12 is a front view explaining the structure of the core tube in FIG. 10, according to an embodiment. FIG. 13 is a schematic cross-sectional view explaining the relation of a plurality of gaps in the joint portion, according to an embodiment.

The medical device 1 illustrated in FIGS. 8-13 is an endoscopic surgical instrument used for endoscopic surgery or the like, and also used in a surgical assist robot. As illustrated in FIG. 8, the medical device 1 may include a rod-like portion 10 located on the side of the surgical assist robot, the surgical device 25 used for endoscopic surgery or the like, and the joint portion 30 located between the rod-like portion 10 and the surgical device 25.

The rod-like portion 10 is a member that extends in a cylindrical shape to be attached to the surgical assist robot. The embodiment illustrated in FIG. 8 is described referring to application to an example in which the rod-like portion 10 is formed in a cylindrical shape having an internal space (not illustrated) through which the cable 121 for the surgical device and the wires 61 for the joint portion, which will be described later, pass. Note that, for simplicity of explanation, the direction in which the central axis CL of the rod-like portion 10 extends will be referred to as an X direction, a direction perpendicular to the X direction will be referred to as a Y direction, and a direction perpendicular to the X direction and the Y direction will be referred to as a Z direction.

The surgical device 25 is located at the leading (i.e., distal) end of the joint portion 30, that is in other words, an end thereof on the positive side in the X direction. In addition, the position and the posture of the surgical device 25 relative to the rod-like portion 10 are controlled by bending of the joint portion 30. The embodiment illustrated in FIG. 8 is described referring to application to an example in which the surgical device 25 is forceps on which opening and closing operations are performed with the cable (wire) 121 for the surgical device. Alternatively, the surgical device 25 may be devices other than forceps used for endoscopic surgery or the like, and is not limited to a specific device type. In addition, cables may be used instead of the wires 61 for the joint portion.

The joint portion 30 is a member formed in a cylindrical or columnar shape at the leading end of the rod-like portion 10 attached to the surgical assist robot, that is in other words, an end thereof on the positive side in the X direction. In addition, the joint portion 30 is capable of being bent in an arc shape in the Y direction, being bent in an arc shape in the Z direction, and being bent in an arc shape in a direction of combination of the Y direction and the Z direction by operation of the wires 61 for the joint portion, which will be described later.

As illustrated in FIG. 9, the joint portion 30 may include an outer shell portion (outer shell member) 131, a core tube 141, a resin tube 151, and the wires 61 for the joint portion. The outer shell portion 131 is formed in a cylindrical shape constituting the external shape of the joint portion 30, and attached to the rod-like portion 10 and the surgical device 25. The outer shell portion 131 has a structure allowing the bending in an arc shape in the Y direction, the bending in an arc shape in the Z direction, and the bending in an arc shape in a direction of combination of the Y direction and the Z direction, and allowing expansion and contraction in the X direction only. In addition, examples of the material for the outer shell portion 131 may include a metal material and a resin material.

As illustrated in FIGS. 9 and 10, the outer shell portion 131 includes a rod-like portion side end 32 to which the rod-like portion 10 is attached, and a surgical device side end 33 to which the surgical device 25 is attached. The rod-like portion side end 32 is an end on the negative side in the X direction of the outer shell portion 131, and the surgical device side end 33 is an end on the positive side in the X direction of the outer shell portion 131. The rod-like portion side end 32 and the surgical device side end 33 each have a stepped portion 34 used for attachment of the rod-like portion 10 or the surgical device 25.

A region of the outer shell portion 131 between the rod-like portion side end 32 and the surgical device side end 33 is a region that may be bent in an arc shape. The embodiment illustrated in FIGS. 9-10 is described referring to application to an example in which a plate-like member 135 extending substantially along the Y-Z plane is arranged around the longitudinal direction of the outer shell portion 131 (in other words, part of the central axis CL corresponding to the outer shell portion 131) while being shifted from one of the rod-like portion 10 side and the surgical device 25 side thereof to the other (in other words, in a helical manner). Note that the region is not limited to have a specific shape as long as the region is bendable in an arc shape.

As illustrated in FIGS. 9 and 10, the outer shell portion 131 has a first through-hole (space) 36 and second through-holes 37 extending in the longitudinal direction of the outer shell portion 131 (in other words, the X direction in a case where the outer shell portion 131 is arranged to extend linearly) through the outer shell portion 131.

The first through-hole 36 is a through-hole extending along part of the central axis CL corresponding to the outer shell portion 131. The core tube 141, the resin tube 151, and the cable 121 for the surgical device may be arranged in the first through-hole 36. In addition, the inner face of the first through-hole 36 supports the core tube 141 from the outer side.

The second through-holes 37 are through-holes formed at positions on a circle around the central axis CL at equal distance therefrom. In other words, the second through-holes 37 are through-holes formed at a total of four positions, which are positions on the positive side and the negative side in the Y direction from the first through-hole 36 and positions on the positive side and the negative side in the Z direction from the first through-hole 36. The wires 61 for the joint portion may be arranged in the four second through-holes 37.

The second through-holes 37 each have, at an end on the surgical device 25 side (on the positive side in the X direction) thereof, an enlarged diameter portion 38 having a larger diameter than the remaining part of the second through-hole 37. Stopping ends 62 of the wires 61 for the joint portion are placed in the enlarged diameter portions 38.

While the embodiment illustrated in FIGS. 9-10 is described referring to application to an example in which four second through-holes 37 are formed, the number of second through-holes 37 is not limited as long as the outer shell portion 131 may be bent in given directions.

As illustrated in FIGS. 10 to 12, the core tube 141 is a cylindrical member having an outer diameter smaller than that of the outer shell portion 131, and arranged inside the first through-hole 36 of the outer shell portion 131. In a manner similar to the outer shell portion 131, the core tube 141 has a structure allowing the bending in an arc shape in the Y direction, the bending in an arc shape in the Z direction, and the bending in an arc shape in a direction of combination of the Y direction and the Z direction.

In addition, the core tube 141 has a higher compression stiffness, and smaller expansion and contraction due to compression force or tension in the X direction than the outer shell portion 131. For example, the core tube 141 is made of a metal material containing at least nickel and titanium as components, or a nickel-titanium alloy, so as to increase the compression stiffness of the core tube 141.

The core tube 141 has a plurality of slits 42, which are narrow cuts, extending in the circumferential direction on a lateral face (circumferential face) thereof. On the lateral face of the core tube 141, two slits 42 extending for almost a semiperimeter of the lateral face are formed at the same position (the same height) on the central axis CL, that is in other words, the X direction. Columns 43, which are part of the lateral face of the core tube 141 are formed between the two slits 42.

A plurality of sets of two slits 42 (hereinafter also referred to as "sets of slits 42"), each being a set of two slits 42 as described above, are arranged at intervals D along the central axis CL, which is the longitudinal direction of the core tube 141. The intervals D have the same value from the end of core tube 141 on the rod-like portion 10 side (the end on the negative side in the X direction) to the end thereof on the surgical device 25 side (the end on the positive side in the X direction).

In other words, the sets of slits 42 are arranged at regular intervals in the longitudinal direction of the core tube 141. The sets of slits 42 include sets of slits 42 in which two slits 42 are arranged in the Y direction, and sets of slits 42 in which two slits 42 are arranged in the Z direction. The sets in which the slits 42 are arranged in the Y direction and the sets in which the slits 42 are arranged in the Z direction are arranged alternately.

As illustrated in FIGS. 9 and 10, the resin tube 151 is a member formed in a cylindrical shape and arranged inside the core tube 141. The cable 121 for the surgical device is inserted through the resin tube 151.

The resin tube 151 is made of a material having a smaller coefficient of friction with respect to the cable 121 for the surgical device than that of the material of the core tube 141. An example of the material of the resin tube 151 may be a material with a small coefficient of friction and a high heat resistance, such as polytetrafluoroethylene (PTFE).

In addition, the resin tube 151 also guides the cable 121 for the surgical device, which is located inside the resin tube 151, to be arranged coaxially with or near the central axis CL of the joint portion 30 (hereinafter also referred to as "near the central axis CL"). For example, when the joint portion 30 has a posture extending coaxially with the rod-like portion 10 (a posture extending linearly), the resin tube 151 guides the cable 121 for the surgical device to be arranged near the central axis CL extending in the X direction. When the joint portion 30 is bent, the resin tube 151 guides the cable 121 for the surgical device to be arranged near the central axis CL of the bent joint portion 30.

In addition, as illustrated in FIG. 13, a gap DA between the core tube 141 and the resin tube 151 is made to be smaller than a gap DC between the outer shell portion 131 and the core tube 141 (gap DA<gap DC). A gap DB between the resin tube 151 and the cable 121 for the surgical device is made to be smaller than the gap DC between the outer shell portion 131 and the core tube 141 (gap DB<gap DC).

Next, the operation of the medical device 1 having the aforementioned structure as illustrated in FIGS. 8-13 will be described. Specifically, the bending movements of the joint portion 30 and manipulation of the surgical device 25 will be explained with reference to FIGS. 8 and 9.

For example, for bending the joint portion 30 toward the positive side in the Y direction, at least one of a pair of wires 61 for the joint portion arranged in the Y direction (wires 61 for the joint portion illustrated in the cross section in FIG. 9) among the four wires 61 for the joint portion is manipulated.

Specifically, an operation of pulling the wire 61 for the joint portion arranged on the positive side in the Y direction toward the rod-like portion 10 (toward the negative side in the X direction) is performed. An operation of proactively feeding the wire 61 for the joint portion arranged on the negative side in the Y direction toward the surgical device 25 (toward the positive side in the X direction) may be performed, or an operation of feeding the wire 61 for the joint portion arranged on the negative side in the Y direction accompanying bending of the joint portion 30 may be performed. Furthermore, for controlling the bending state of the joint portion 30, tension pulling the wire 61 for the joint portion toward the rod-like portion 10 may be applied while the wire 61 for the joint portion is fed toward the surgical device 25 (toward the positive side in the X direction).

The joint portion 30 is bent in an arc shape by manipulation of a wire 61 for the joint portion. In this process, the compression stiffness of the core tube 141 suppresses contraction of the joint portion 30 in the X direction caused by the operation of pulling the wire 61 for the joint portion. In addition, because the core tube 141 having an outer dimeter smaller than that of the outer shell portion 131 is arranged inside the first through-hole 36 of the outer shell portion 131, a change in the length of the joint portion 30 along the central axis CL caused by bending is reduced.

For returning the bent joint portion 30 back to the posture extending in the X direction, an operation of pulling the wire 61 for the joint portion arranged on the negative side in the Y direction toward the rod-like portion 10 (toward the negative side in the X direction) is performed.

For bending the joint portion 30 in an arc shape in the Z direction, at least one of a pair of wires 61 for the joint portion arranged in the Z direction among the four wires 61 for the joint portion is manipulated. For bending the joint portion 30 in an arc shape in a direction of combination of the Y direction and the Z direction, at least two of the four wires 61 for the joint portion are manipulated.

Manipulation of the surgical device 25 of the medical device 1 is performed by manipulation of the cable 121 for the surgical device. For example, an operation of pulling the cable 121 for the surgical device toward the rod-like portion 10 (toward the negative side in the X direction) is performed. The method of manipulating the cable 121 for the surgical device may be changed as appropriate depending on the type of the surgical device 25, and is not limited to manipulations described above.

According to the structure described above, the combination of the outer shell portion 131, the core tube 141, and the resin tube 151 enables easier achievement of user-friendliness of the joint portion 30 and the surgical device 25.

Specifically, the combination of the outer shell portion 131 and the core tube 141 facilitates bending of the joint portion 30 as a whole in an arc shape, and makes it easy to achieve user-friendliness of the joint portion 30. This combination also prevents the joint portion 30 from having an insufficient compression stiffness, and makes it easy to achieve user-friendliness of the surgical device 25.

Furthermore, combination of the resin tube 151 facilitates positioning of the cable 121 for the surgical device, to be used for manipulation of the surgical device 25, near the central axis CL of the joint portion 30. This combination facilitates suppression of a change in the path length of the cable 121 for the surgical device when the joint portion 30 is bent, and further makes it easy to achieve user-friendliness of the surgical device 25. Furthermore, because the resin tube 151 has a small coefficient of friction with respect to the cable 121 for the surgical device, manipulation of the cable 121 for the surgical device is facilitated, and user-friendliness of the surgical device 25 may be easily achieved.

Because a plurality of slits 42 are arranged at regular intervals along the central axis CL, which is the longitudinal direction of the core tube 141, the flexibility of the joint portion 30 in the longitudinal direction is more likely to be uniform and the user-friendliness of the joint portion 30 is more easily achieved than those in a case where the intervals between slits 42 are irregular.

Because the outer shell portion 131 is formed of an outer shell plate formed in a belt-like shape and arranged helically, the size of the joint portion 30 in the direction of the central axis CL, which is the longitudinal direction thereof, may be easily made smaller as compared with a case where outer shell plates formed in a disc-like shape are arranged in the longitudinal direction.

Because the core tube 141 is made of a metal material containing at least nickel and titanium as components, sufficient compression stiffness and bending flexibility of the core tube 141 are more easily achieved as compared with a case where the core tube 141 is made of other metal materials.

Because the gap DA between the core tube 141 and the resin tube 151 is made to be smaller than the gap DC between the outer shell portion 131 and the core tube 141, the joint portion 30 may be more easily bent and the user-friendliness of the joint portion 30 is more easily achieved as compared with a case where the gap DA is larger than the gap DC.

Because the gap DB between the resin tube 151 and the cable 121 for the surgical device is made to be smaller than the gap DC between the outer shell portion 131 and the core tube 141, a change in the path length of the cable 121 for the surgical device when the joint portion 30 is bent is more easily suppressed and the user-friendliness of the surgical device 25 is more easily achieved as compared with a case where the gap DB is larger than the gap DC.

<Bending Movement of Joint Portion 30 of Forceps Device K>

With the structure as described above, the forceps device K illustrated in FIG. 6 may bend the joint portion 30 in an arc shape toward the positive side in the Y direction, in an arc shape toward the negative side in the Y direction, in an arc shape toward the positive side in the Z direction, and in an arc shape toward the negative side in the Z direction.

<Grasping Movement by Link Structure of Forceps Device K>

With the structure described above, in the forceps device K illustrated in FIG. 7, when the cable 121 for the surgical device is fed in the direction of an arrow α1, a link structure 40 connecting the cable 121 for the surgical device with the grasping unit 27 moves the grasping portion 27*b* in the direction of an arrow β1. As a result, the grasping portions 27*a* and 27*b* of the grasping unit 27 open.

In contrast, when the cable 121 for the surgical device is pulled in the direction of an arrow α2, the grasping portion 27*b* moves in the direction of an arrow β2. As a result, the grasping portions 27*a* and 27*b* of the grasping unit 27 close and may thus grasp an object.

<Relation Between Cable 121 for Surgical Device and Wires 61 for Joint Portion in Forceps Device K and Cable 35*b* and Wires 35*a* and 35*c* in Housing 20>

In the forceps device, one cable and four wires 61 for the joint portion are used, which have different roles. For example, the cable 121 for the surgical device corresponds to extension of the cable 35*b* in the housing 20 through the shaft 111. A pair of wires 61 for the joint portion arranged in the Y direction correspond to extension of a pair of wires 35*a* in the housing 20 through the shaft 111. A pair of wires 61 for the joint portion arranged in the Z direction correspond to extension of a pair of wires 35*c* in the housing 20 through the shaft 111.

The driving force from the power unit 104, in which pistons like pneumatic actuators linearly move, linearly moves the drive elements 31 in the housing 20. As a result, the wires are pulled in predetermined directions, which allows the bending movements of the forceps device. In addition, the cable is fed or pulled in predetermined directions, which allows the grasping movements of the forceps device. In the surgical device 100, the movements of individual components of the forceps device K are controlled via the two wires (two braided wires) and one cable.

Operations and Effects

The surgical device 100 includes the forceps device K capable of performing bending movements, and opening and closing movements of the grasping portions thereof, the drive elements 31*a*, 31*b*, and 31*c* to which driving force is transmitted from outside, and the wire 35*a*, the cable 35*b*, and the wire 35*c* fixed to the drive elements 31*a*, 31*b*, and 31*c*, respectively, to transmit linear movements of the drive elements 31*a*, 31*b*, and 31*c* to the forceps device K. The forceps device K includes the joint portion 30 that performs bending movements when the wires 35*a* and 35*c* are pulled, and the link structure 40 that performs opening and closing movements when the cable 35*b* is moved.

Thus, linear movements of the drive elements 31*a*, 31*b*, and 31*c* may be transmitted to the forceps device K via the wires 35*a* and 35*c* and the cable 35*b*. When the wires 35*a* and 35*c* are pulled, a bending movement is performed. When the cable 35*b* moves, the opening and closing movements are performed. In addition, because the movements of the drive elements 31*a*, 31*b*, and 31*c* transmitted by the wires 35*a* and 35*c* and the cable 35*b* are linear, the structure of the drive elements 31*a*, 31*b*, and 31*c* may be made simple.

In addition, a plurality of driven portions are the drive element 31*a*, the drive element 31*b*, and the drive element 31*c*. A plurality of cords are the wire 35*a* for bending movement fixed to the drive element 31*a*, the cable 35*b* for opening and closing operations fixed to the drive element 31*b*, and the wire 35*c* for bending movement fixed to the drive element 31*c*. Thus, the movements of the drive elements 31*a*, 31*b*, and 31*c* may be individually controlled, which enables the bending movements and the opening and closing movements of the forceps device K to be controlled independently of each other.

The drive elements 31*a*, 31*b*, and 31*c* each linearly move in the first direction (the Z direction in FIG. 4), that is, in parallel with each other, and are arranged in a second direction (the X direction in FIG. 4) intersecting the first direction. This configuration prevents the linear movement of each of the drive elements 31*a*, 31*b*, and 31*c* from interfering with the movements of the other drive elements. In addition, the arrangement of the drive elements 31*a*, 31*b*, and 31*c* in the second direction facilitates the layout of the drive elements 31*a*, 31*b*, and 31*c*.

The forceps device K is structured to perform a first bending movement, a second bending movement in a direction different from the first bending movement by the movements of the wires 35*a* and 35*c*, and the opening and closing movements by the movements of the cable 35*b*. As a result, complicated movements of the forceps device K may be achieved by linear movements of the wires and the cable.

Note that the technical scope of the present disclosure is not limited to the various embodiments described above, and various modifications may be made without departing from the scope of the appended claims.

What is claimed is:

1. A surgical device comprising:

a forceps device configured to perform a bending movement, and configured to perform opening and closing movements of grasping portions of the forceps device;

a housing configured to be detachably attached to an adapter of a surgical robot;

a plurality of driven portions located in the housing and configured to be linearly driven by a driving force that is transmitted from outside the surgical device via the adapter; and a plurality of cords, each being fixed to one of the plurality of driven portions, the plurality of cords transmitting respective linear movements of the plurality of driven portions to the forceps device, wherein the forceps device includes a joint portion that is configured to perform the bending movement when a cord for the bending movement among the plurality of cords is pulled, and a link structure that is configured to perform the opening and closing movements when a cord for the opening and closing movements among the plurality of cords is moved.

2. The surgical device according to claim 1, wherein the joint portion comprises:

an outer shell that is cylindrical;

a first through hole that is coaxial with the outer shell, the cord for the opening and closing movements passing through the first through hole; and a second through hole disposed between the first through hole and the outer shell, the cord for the bending movement passing through the second through hole.

3. The surgical device according to claim 1, wherein the plurality of cords include a first wire for a first bending movement, a cable for the opening and closing movements, and a second wire for a second bending movement, and wherein the joint portion comprises:

an outer shell that is cylindrical;

a first through hole that is coaxial with the outer shell, the cable passing through the first through hole; and a plurality of second through holes disposed between the first through hole and the outer shell, the first wire and the second wire passing through a respective one of the plurality of second through holes.

4. The surgical device according to claim 1, wherein the housing comprises a plurality of openings through which the driving force is transmitted to the plurality of driven portions via the adapter.

5. The surgical device according to claim 1, wherein the plurality of cords include a cable for the opening and closing movement and a plurality of wires for the bending movement, and wherein the joint portion comprises:

an outer shell that is cylindrical;

a first through hole that is coaxial with the outer shell, the cable passing through the first through hole; and a plurality of second through holes disposed between the first through hole and the outer shell, the plurality of wires passing respectively through the plurality of second through holes.

6. The surgical device according to claim 5, wherein the plurality of second through holes are radially spaced apart from one another around the first through hole.

7. The surgical device according to claim 1, wherein:

the plurality of driven portions include a first driven portion, a second driven portion, and a third driven portion, and the plurality of cords include a first wire for the bending movement fixed to the first driven portion, a cable for the opening and closing movements fixed to the second driven portion, and a second wire for the bending movement fixed to the third driven portion.

8. The surgical device according to claim 7, wherein the forceps device is configured to perform:

a first bending movement;

a second bending movement in a direction that is different from a direction of the first bending movement; and the opening and closing movements, wherein the first bending movement and the second bending movement are caused by movements of the first wire for the bending movement and the second wire for the bending movement, respectively, and wherein the opening and closing movements are caused by movements of the cable for the opening and closing movements.

9. The surgical device according to claim 7, wherein the first driven portion, the second driven portion, and the third driven portion linearly move in parallel with each other in a first direction, and are arranged in a second direction that intersects the first direction, and wherein the first driven portion, the second driven portion, and the third driven portion are each arranged in a respective one of three long holes of the housing, and the first driven portion, the second driven portion, and the third driven portion are arranged relative to each other in the second direction as viewed in a direction in which the housing is attached to and detached from the adapter.

10. The surgical device according to claim 9, wherein the forceps device is configured to perform:

a first bending movement;

a second bending movement in a direction that is different from a direction of the first bending movement; and the opening and closing movements, wherein the first bending movement and the second bending movement are caused by movements of the first wire for the bending movement and the second wire for the bending movement, and wherein the opening and closing movements are caused by movements of the cable for the opening and closing movements.

11. A surgical device comprising:

a forceps device;

a housing configured to be detachably attached to an adapter of a surgical robot;

a plurality of driven portions located in the housing and configured to be linearly driven by a driving force that is transmitted from outside the surgical device via the adapter;

a plurality of wires, each being fixed to one of the plurality of driven portions, the plurality of wires transmitting respective linear movements of the plurality of driven portions to the forceps device, wherein the forceps device comprises:

a plurality of grasping portions configured to be opened and closed by a movement of a first wire of the plurality of wires; and a joint portion configured to bend by a movement of at least one second wire of the plurality of wires.

12. The surgical device according to claim 11, wherein:

the at least one second wire includes a plurality of second wires, the plurality of driven portions include a first driven portion, a second driven portion, and a third driven portion, and the first wire is fixed to the first driven portion that opens and closes the plurality of grasping portions, one of the plurality of second wires is fixed to the second driven portion that bends the forceps device in a first direction, and another of plurality of second wire is fixed to the third driven portion that bends the forceps device in a second direction different from the first direction.

13. The surgical device according to claim 12, wherein the first driven portion, the second driven portion, and the third driven portion linearly move in parallel with each other in the first direction, and are arranged in the second direction that intersects the first direction, and wherein the first driven portion, the second driven portion, and the third driven portion are each arranged in a respective one of three long holes of the housing, and the first driven portion, the second driven portion, and the third driven portion are arranged relative to each other in the second direction as viewed in a direction in which the housing is attached to and detached from the adapter.

14. The surgical device according to claim 11, wherein the joint portion comprises:

an outer shell that is cylindrical;

a first through hole that is coaxial with the outer shell and through which the first wire passes; and a second through hole disposed between the first through hole and the outer shell and through which the at least one second wire passes.

15. The surgical device according to claim 11, wherein the at least one second wire includes two second wires, and wherein the joint portion comprises:

an outer shell that is cylindrical;

a first through hole that is coaxial with the outer shell and through which the first wire passes; and two second through holes disposed between the first through hole and the outer shell, the two second wires passing through respective ones of the two second through holes.

16. The surgical device according to claim 11, wherein the at least one second wire includes a plurality of second wires, and wherein the joint portion comprises:

an outer shell that is cylindrical;

a first through hole that is coaxial with the outer shell and through which the first wire passes; and a plurality of second through holes disposed between the first through hole and the outer shell, the plurality of second wires passing through respective ones of the plurality of second through holes.

17. The surgical device according to claim 16, wherein the plurality of second through holes are radially spaced apart from one another around the first through hole.

18. The surgical device according to claim 12, wherein the first driven portion, the second driven portion, and the third driven portion linearly move in parallel with each other in the first direction, and wherein the first driven portion, the second driven portion, and the third driven portion are arranged relative to each other in the second direction such that the first driven portion, the second driven portion, and the third driven portion do not overlap with each other as viewed in a direction in which the housing is attached to and detached from the adapter.

* * * * *